(12) United States Patent
Eriksson et al.

(10) Patent No.: US 11,779,727 B2
(45) Date of Patent: Oct. 10, 2023

(54) URINARY CATHETER ASSEMBLY (71) Applicant: DENTSPLY IH AB, Mölndal (SE)

(72) Inventors: Karsten Eriksson, Fotö (SE); Michael Sandberg, Askim (SE); Niklas Dahlberg, Lerum (SE); Benny Svendsen, Gothenburg (SE)

(73) Assignee: DENTSPLY IH AB, Mölndal (SE)

( * ) Notice: Subject to any disclaimer, the term of this patent is extended or adjusted under 35 U.S.C. 154(b) by 10 days.

(21) Appl. No.: 17/511,431

(22) Filed: Oct. 26, 2021

(65) Prior Publication Data
US 2022/0126057 A1   Apr. 28, 2022

(30) Foreign Application Priority Data

Oct. 27, 2020 (EP) .................................. 20204166

(51) Int. Cl.
*A61M 25/00* (2006.01)

(52) U.S. Cl.
CPC ...... *A61M 25/002* (2013.01); *A61M 25/0017* (2013.01)

(58) Field of Classification Search
CPC ............ A61M 25/002; A61M 25/0017; A61M 2025/0175; A61M 25/0113; A61M 25/0111; A61M 2025/0046; A61M 25/01; A61M 25/0009; A61M 2202/0496; A61M 2210/1085; A61M 25/10; A61M 25/0028; A61M 25/0097; A61M 2025/0004; A61M 25/0662; A61M 2025/0681; A61M 25/0043; A61F 5/44; A61F 2013/15146; A61F 2002/047; B29L 2031/7542; A61B 50/30

See application file for complete search history.

(56) References Cited

U.S. PATENT DOCUMENTS 3,807,408 A * 4/1974 Summers .......... A61M 25/0017
                                                    604/104
4,598,834 A * 7/1986 Singletary, Jr. ........... A61J 1/10
                                                    53/425

(Continued)

FOREIGN PATENT DOCUMENTS

| EP | 0093093 A1 | 11/1983 |
| EP | 0217771 A1 | 4/1987 |
| EP | 2823845 A1 | 1/2015 |

*Primary Examiner* — Nicholas J. Weiss
*Assistant Examiner* — Brandon W. Levy
(74) *Attorney, Agent, or Firm* — Perkins Coie LLP (57) ABSTRACT

A urinary catheter assembly includes a urinary catheter having a proximal part with an insertion tip, a distal part and a tubular shaft extending between the insertion tip and the distal part. A package having at least a first compartment with an opening is provided to enclose the proximal part and at least a part of the tubular shaft therein in a curved or curled state during storage. A protective sleeve arrangement is arranged around the distal part of the urinary catheter, and a distal end of the protective sleeve arrangement is connected to the urinary catheter, at or in the vicinity of a distal end of the catheter. The protective sleeve arrangement includes at least two sleeves that are telescopically displaceable in relation to each other, and the protective sleeve arrangement is transformable between a retracted position and an extended position.

19 Claims, 4 Drawing Sheets

(56) References Cited

U.S. PATENT DOCUMENTS

| | | | | |
|---|---|---|---|---|
| 5,846,259 | A | * 12/1998 | Berthiaume | A61M 25/00 |
| | | | | 606/191 |
| 9,987,464 | B1 | 6/2018 | Donald et al. | |
| 2006/0025753 | A1 | 2/2006 | Kubalak et al. | |
| 2006/0184105 | A1* | 8/2006 | Townsend | A61M 25/0141 |
| | | | | 604/93.01 |
| 2015/0018803 | A1* | 1/2015 | Tjassens | A61M 25/002 |
| | | | | 604/544 |
| 2016/0193447 | A1* | 7/2016 | Matthiassen | A61M 39/22 |
| | | | | 604/544 |
| 2017/0173300 | A1* | 6/2017 | Hannon | A61M 25/0097 |
| 2018/0126121 | A1* | 5/2018 | Mauch | A61F 2/2427 |
| 2019/0046767 | A1 | 2/2019 | Palmer | |

* cited by examiner

URINARY CATHETER ASSEMBLY

CROSS REFERENCE TO RELATED APPLICATION

This patent document claims the benefits and priority of European Patent Application No. 20204166.1, filed on Oct. 27, 2020, which is incorporated herein by reference in its entirety.

TECHNICAL FIELD OF THE INVENTION

The disclosed embodiments relate to urinary catheter assemblies, and in particular to hydrophilic urinary catheter assemblies.

BACKGROUND

The disclosed embodiments relate to urinary catheter assemblies. Urinary catheters are commonly used for draining urine from the bladder. Urinary catheters can be of an indwelling type, for long term use, such as days or even weeks, or for intermittent use, whereby the catheters are used for a single draining procedure, typically lasting a few minutes. Intermittent urinary catheters are e.g., used by a large group of persons for self-catheterization, which is a daily-life procedure, taking place several times a day. Typically, catheters for intermittent catheterization are used by patients suffering from urinary retention, due to e.g. spinal cord injury, Multiple Sclerosis or Prostatic Hyperplasia. Using an intermittent catheter, the bladder may be drained through a natural or artificial urinary canal. Many catheters, such as those for intermittent catheterization, are provided with a hydrophilic coating or the like, providing a smooth and slippery surface when wetted, for safe and comfortable insertion in the urinary canal.

SUMMARY

This section is intended to provide a summary of certain example embodiments and is not intended to limit the scope of the embodiments that are disclosed in this application.

The disclosed embodiments, among other features and benefits, describe improved urinary catheter assemblies, and in particular male urinary catheter assemblies. According to a first aspect of the disclosed embodiments, there is provided a urinary catheter assembly that includes a urinary catheter having a proximal part with an insertion tip, a distal part and a tubular shaft extending there between, wherein the distal part, on a least a part thereof, has a greater cross-sectional dimension than the tubular shaft and the proximal part. The urinary catheter assembly includes a package having at least a first compartment with an opening, said first compartment being arranged to enclose the proximal part and at least a part of the tubular shaft therein, and wherein the part of the urinary catheter being arranged in the first compartment is arranged in a curved or curled state during storage. The urinary catheter assembly also includes a protective sleeve arrangement arranged around the distal part of the urinary catheter, a distal end of the protective sleeve arrangement being connected to the urinary catheter, at or in the vicinity of a distal end thereof. The protective sleeve arrangement comprises at least two sleeves being telescopically displaceable in relation to each other, wherein the protective sleeve arrangement is transformable between a retracted position and an extended position.

In the present application, the term "proximal" is used to indicate the end or portion of a catheter that is inserted into the body of the user, i.e., the end or portion of the catheter that during use is closer in proximity to the user's body and/or initially enters the user's body upon insertion. The term "distal" is used to refer to an end or portion of the catheter that is opposite the proximal end or portion and is typically further away from the user's body. For the sake of consistency, when the terms "distal" and "proximal" are used in the context of other components, such as protective sleeve arrangement and its sleeves, which are not intended for introduction into the user's body, these terms are used in an analogous way. For such other components, "proximal" refers to the end or portion that is closer to the proximal end of the catheter when the catheter is housed within the assembly, while "distal" refers to an end or portion located opposite to such proximal end or portion.

The catheter is arranged in a curved or curled state. A curved or curled state here means that the catheter is arranged in a non-straight disposition, such as being bent, folded, or otherwise curved or curled. Preferably, the curved or curled state in total forms at least a 180 degrees curvature.

Since the catheter inside the first compartment of the package is arranged in a curved or curled state, the length of the first compartment, and also the entire package, can be much shorter than the ordinary length of the catheter. In particular for male catheters, which conventionally has a length of about 40 cm, this is of great advantage, since the assembly of the disclosed catheters can have a length of less than 25 cm, and preferably less than 20 cm, less than 15 cm, or even shorter. This makes it easy to carry the urinary catheter assembly in a discreet way, e.g., in a small bag, a pocket, or the like. Thus, the present urinary catheter assembly can be made very compact.

However, when a catheter is stored in a curled or curved shape, it generally retains this shape even after extraction from the catheter, due to the memory of the material. Thus, it is a well-known problem that catheters having been stored in a curled or curved shape are generally difficult to handle, and in particular it is difficult to manipulate the catheter for insertion into the urethra in a clean and safe manner.

In the new urinary catheter assembly, this problem is efficiently overcome. Upon extraction of the catheter from the package/first compartment, the user pulls out the distal end, and extends the protective sleeve arrangement over the extracted catheter shaft. Hereby, the protective sleeve arrangement not only serves as a protection for the catheter shaft, preventing contamination of it, but also serves as an outer reinforcement which straightens the catheter shaft, and maintains the catheter shaft in this straight condition during manipulation and insertion of the catheter into the urethra. In addition, this provides a reinforcement of the catheter, which prevents bending and kinking of the catheter as it is pushed into the urethra. Thus, even though the catheter is basically pushed from its rearward, distal side, it maintains its shape and rigidity by the reinforcing outer wall surrounding it, provided by the protective sleeve arrangement.

In the storage state, the protective sleeve arrangement is in a retracted, compacted state, and covers only a very limited part of the catheter, such as the distal part of the catheter. The remainder of the catheter, including the insertable part of the catheter shaft, resides in the first compartment of the package. During, or after, extraction of the catheter from the package/first compartment, the protective sleeve arrangement is extended into its extended state. In this state, the protective sleeve arrangement covers a significant length of the catheter shaft, including a significant length of the insertable part. Preferably, the protective sleeve arrangement in this extended state covers at least 60% of the length of the catheter shaft, and preferably at least 70%, and more preferably at least 80%, and more preferably at least 90%, and more preferably at least 90%, and most preferably at least 95%. However, the protective sleeve arrangement may still be at least slightly shorter than the length of the catheter shaft, even in the extended state, so that a part of the catheter shaft extends out from the extended protective sleeve arrangement, to facilitate insertion of the catheter. Thus, the length of the protective sleeve arrangement may be less than 99% of the length of the catheter shaft, and more preferably less than 95%. For example, the length of the protective sleeve arrangement may be in the range of 50-100% of the length of the catheter shaft, and preferably in the range of 60-99%, and most preferably in the range of 60-95%.

Hereby, a small part of the catheter shaft extends out from the extended protective sleeve arrangement after extraction of the catheter from the package/first compartment. However, alternatively, the protective sleeve arrangement may have a length being essentially equal to the length of the catheter shaft.

In the extended position, the user may use the extended protective sleeve arrangement as a handle, and grip the protective sleeve arrangement for clean manipulation and insertion of the catheter in order to guide it into the urethra. Due to the significant length of the protective sleeve arrangement, it is easy and convenient to grip. Further, the catheter shaft is maintained in a relatively straight state by the protective sleeve arrangement, thereby facilitating insertion of the catheter. Since only the protective sleeve arrangement need to be touched, the risk of contaminating the catheter during this procedure is greatly alleviated.

As the catheter is inserted into the urethra, the protective sleeve arrangement may again be compacted into its retracted state, thereby allowing the entire insertable length of the catheter shaft to be inserted. The compaction of the protective sleeve arrangement may here be obtained by manually moving the telescopic sleeves of the protective sleeve arrangement together, or automatically, by simply pulling the proximal end of the protective sleeve arrangement to the glans of the penis during insertion.

After use, when the catheter is expelled from the urethra, the protective sleeve arrangement may again be enlarged, into its extended state, to facilitate handling of the catheter in a clean manner during subsequent activities, such as cleaning of the catheter, discarding of the catheter, or rearrangement of the catheter into the package.

Thus, the new urinary catheter assembly present a compact and neat storage position. In this position, the catheter assembly could easily be carried around discretely, e.g., in a handbag, in a pocket or the like, without attracting notice. Further, the catheter assembly can easily be transformed into the extended position, in which the protective sleeve arrangement is extended upon extraction of the catheter, for use as a catheter insertion aid, as discussed in the foregoing. After use, the catheter assembly may be directly discarded. However, it may alternatively be returned to the closed position, so that the used catheter assembly can then be carried by the user in the same discrete way as the unopened assembly, and without the risk of spillage etc., to be discarded later.

The distal part may have, at least partly, an enlarged diameter compared to the catheter shaft. The distal part may comprise of form a funnel shaped or flared connector. The connector may e.g., be a Standard Interface Connector (SIC). However, urine may also be discharged out from the distal part directly into a toilet or the like, and need for such applications not be provided with any connection interface.

In one embodiment, at least the distal part of the urinary catheter may form an extending part, extending out from the first compartment through the opening of the first compartment. In such embodiments, the distal part may be arranged in a second compartment of the package, or be entirely outside the package.

Further, a proximal end of the protective sleeve arrangement may be releasably connected to the package, at or in the vicinity of the opening of the first compartment. Hereby, the protective sleeve arrangement may automatically be extended to its extended position when the catheter is pulled out from the first compartment.

The package may be formed of a sheet material, such as a foil. The package is preferably capable of maintaining the interior in a sterile state. Further, the package, and in particular the first compartment, is preferably liquid impermeable, and most preferably made of a gas impermeable material. For example, the material may be a laminate, comprising a layer of a gas and/or liquid barrier material, such as $SiO_x$, $AlO_x$ or a metal layer or metallized layer. It is also feasible to provide an outer container, such as a pouch, enclosing the package. In this case, the container and the package may in combination provide sufficient liquid and/or gas impermeability, even though neither the package nor the container are per se sufficiently gas and/or liquid impermeable.

The catheter may be a hydrophilic catheter, having a hydrophilic surface. The hydrophilic surface may be arranged as a hydrophilic coating arranged on a substrate of the catheter, as is per se well known in the art. However, the hydrophilic surface may alternatively be arranged as an integrated part of the catheter, such as an integrated layer, or alternatively, the entire catheter, or part(s) of the catheter, may be made of a hydrophilic material. The hydrophilic surface is preferably arranged to provide low friction when wetted. The hydrophilic surface may be a surface provided with a hydrophilic coating.

The catheter assembly may further comprise a wetting fluid, such as a wetting liquid, for wetting and activation of the hydrophilic surface. The wetting fluid may be arranged in a separate compartment within the assembly, to be released into the compartment housing the catheter shaft at a suitable time, such as immediately prior to use. This release may be obtained by provision of a certain release action, such as by compressing or twisting the compartment, or automatically following on another action, such as opening of the package/first compartment, initiation of extracting the catheter, or the like. However, the wetting fluid may also be provided within the same compartment as the catheter shaft, thereby maintaining the catheter in a wetted, activated state also during storage. This wetted state may be present immediately following closing and sealing of the package/first compartment, or be obtained after some time of storage. The activated state may thus be provided by pre-wetting of the catheter, prior to arrangement of the catheter in the package/first compartment, but may alternatively be provided after placement of the catheter in the package/first compartment. Specifically, wetting of the hydrophilic surface may occur during a period of storage in a sealed container by provision of a humid atmosphere in the package/first compartment, as is per se known in the art, e.g., by being arranged within a hydration element, such as a chamber or sachet which is liquid impermeable and vapor permeable.

Since the hydrophilic surface is then maintained in a wetted state during storage, the medical device is immediately ready-to-use upon removal from the package/first compartment, and needs not be wetted or treated in any way prior to use. In such embodiments, the package, and at least the first compartment of the package, is preferably impermeable to the wetting fluid, and preferably made of a gas and/or liquid impermeable material. This ensures that moisture does not penetrate out from the package/first compartment during storage, and enhances the shelf-life of the product. In embodiments where the wetting fluid is maintained separated from the catheter during storage, only the compartment holding the wetting fluid need to be gas impermeable.

The wetting fluid may be a wetting liquid, and preferably an aqueous liquid, comprising at least 75% of weight of water, and preferably at least 80% of weight, and more preferably at least 85% of weight, and most preferably at least 90% of weight. In some embodiments, the wetting liquid may be plain water. However, the wetting liquid may also comprise one or more additives, such as an antibacterial agent, a pharmaceutical active substance, or the like.

The catheter is preferably a urinary catheter, and most preferably a urinary catheter for intermittent, short time use. The term "short term use" indicates a use that is limited in time, and in particular limited to a time period of less than 15 minutes, and preferably less than 10 minutes, and most preferably less than 5 minutes.

The protective sleeve arrangement may contain only two sleeves. However, preferably the protective sleeve arrangement comprises at least three sleeves being telescopically displaceable in relation to each other.

Each sleeve may have a length in the range of 4-15 cm, and preferably in the range of 6-13 cm, and most preferably in the range of 8-12 cm. The total extracted length of the protective sleeve arrangement may be in the range of 8-40 cm, and preferably in the range of 20-40 cm, and most preferably in the range of 30-40 cm, such as in the range 35-40 cm.

The sleeves may have equal lengths. However, it is also feasible to use sleeves of different lengths. For example, the outermost sleeve may be longer than the inner sleeves.

A sleeve of said at least two sleeves having the greatest diameter may have an end releasably connected to the first compartment. However, the proximal end of the protective sleeve arrangement may also be loose in relation to the package.

Preferably, a sleeve of said at least two sleeves having the smallest diameter has an end connected to the urinary catheter. Hereby, the protective sleeve arrangement will gradually increase in diameter towards the catheter insertion end when in the extended position. Thus, the protective sleeve arrangement, in its extended position preferably has the sleeve with the smallest diameter arranged closest to the distal end of the catheter, and the sleeve with the largest diameter arranged closest to the proximal end of the catheter. This facilitates both manufacturing and handling, since the smallest sleeve can be connected to the catheter, and the other, larger, sleeves be arranged on the outside of the smallest sleeve. This also provides a sufficiently large opening for the catheter shaft, at the proximal end of the protective sleeve arrangement, avoiding the risk of damaging the hydrophilic surface and the like. Further, the arrangement of the largest sleeve closest to the proximal end of the catheter facilitates handling of the catheter, since it provides an easier and better grip for the user. Further, this arrangement facilitates a safe and reliable connection to the first compartment. However, it is also feasible to connect the sleeve having the largest diameter to the urinary catheter.

The protective sleeve arrangement is preferably relatively rigid, so that it cannot be easily compressed or the like. The rigidity of the protective sleeve arrangement is preferably such that it cannot be bent during ordinary handling of the catheter. It is further preferably such that the protective sleeve arrangement cannot be compressed onto the catheter by moderate, or even high, finger pressure during handling. Preferably, the at least two sleeves of said protective sleeve arrangement each has a rigidity which is greater than the rigidity of the tubular shaft of the urinary catheter. The sleeves are preferably rigid both in an axial direction and in cross-sectional direction, thus resisting deformation in both said directions. By the use of such rigid sleeves, the stabilization of the catheter shaft during insertion is improved. This also enables the use of more flexible, less rigid, catheter shafts than presently used.

The protective sleeve arrangement is preferably releasably connected to the urinary catheter, and wherein the distal part of the urinary catheter is arranged telescopically displaceable in the protective sleeve arrangement. Hereby, the distal part of the urinary catheter, or a part thereof, may be telescoped out from the protective sleeve arrangement during extraction of the catheter from the package/first compartment, so that the protective sleeve arrangement then primarily covers the insertable part of the catheter when in the extended state. Hereby, the protective sleeve arrangement can cover a larger length of the catheter shaft, or alternatively, a shorter protective sleeve arrangement may be used.

The distal part of the urinary catheter, at a proximal part thereof, is preferably provided with an outwardly protruding part, such as a flange, arranged to engage with an inwardly protruding part, such as a flange, of an inner sleeve of said at least two sleeves. Hereby, the distal part will be brought into engagement with the inner sleeve, upon contact between the inwardly protruding part and the outwardly protruding part, thereby forming a connection between the distal part of the catheter and the inner sleeve. This prohibits complete extraction of the distal part from the inner sleeve, and brings the inner sleeve away from the package/first compartment together with the catheter upon continued extraction.

Further, every sleeve being arranged outwardly of any other of the at least two sleeves preferably comprises an inward protrusion at or in the vicinity of a distal end, and wherein every sleeve being arranged inwardly of any other of the at least two sleeves comprises an outward protrusion at or in the vicinity of a proximal end. Hereby, each inner sleeve will be brought into engagement with its closest outer sleeve, upon contact between the inward protrusion and the outward protrusion, thereby forming a connection between the sleeves. This prohibits complete extraction of any sleeve from its adjacent outer sleeve, and brings the sleeves sequentially away from the package/first compartment together with the catheter upon continued extraction, as the protective sleeve arrangement gradually assumes its extended state.

The outward protrusion, or the outwardly protruding part, may be provided as a narrowing section, providing a decreased internal diameter compared to at least an adjacent part, and the inward protrusion, or the inwardly protruding part, may be provided as an expanded section, providing an enlarged external diameter compared to at least an adjacent part. The narrowing sections and the expanded sections may form a stop abutment when brought together.

The first compartment may be provided with an annular recession encircling said opening, said annular recession being arranged to receive and connect to the protective sleeve arrangement when in the retracted position. This facilitates a secure and reliable connection and seal between the protective sleeve arrangement and the first compartment. Further, this enables resealing of the first compartment, in case the catheter is rearranged in the package after use.

The at least two sleeves, and preferably at least three sleeves, are preferably arranged essentially entirely overlying each other in the retracted position.

The sleeves of the protective sleeve arrangement may have circular cross-sections, but alternative shapes, such as rectangular and semi-circular shapes are also feasible.

The urinary catheter assembly may further comprise a removable or openable closure arranged over a drainage opening in a distal end of the urinary catheter, the closure together with the protective sleeve arrangement and the first compartment forming a closed interior space for the catheter, said closed interior space preferably forming a sterile and moisture proof compartment for the catheter. The closure may e.g., comprise a cap or lid arranged to close the drainage opening of the catheter. The cap or lid may further be connected to the catheter by a hinge or the like, so that it remains in place even after being opened. In this case, the cap or lid may also be used as a grip to initiate extraction of the catheter out from the package/first compartment. However, in particular for embodiments where the distal end of the catheter is enclosed in a second compartment of the package, this closure could be omitted. It is also feasible to provide such a closure in the package, e.g., for closing of an opening in the second compartment.

The catheter preferably comprises one or several drainage openings, so-called eyes or eyelets, arranged at or in the vicinity of the proximal insertion end. A part of, or the whole, catheter shaft may form an insertable part or insertable length of the catheter. At least the insertable part may further be provided with a hydrophilic coating, or in other ways been provided with a hydrophilic surface, which exhibits a lowered friction when wetted. Further, the distal part may, at least on a part thereof, have larger cross-sectional dimensions than the catheter shaft. The distal part may e.g., be flared or funnel shaped, increasing in dimension towards the distal end, thereby enabling connection of a tube, collection bag or the like.

According to another aspect of the disclosed embodiment, there is provided a method for preparing a urinary catheter for use. The method includes providing a urinary catheter having a proximal part with an insertion tip, a distal part and a tubular shaft extending there between in a package with a first compartment having an opening, wherein at least the distal part of the urinary catheter preferably forms an extending part extending out from the first compartment of the package through said opening, the part of the urinary catheter being arranged in the first compartment being arranged in a curved or curled state during storage. The method also includes providing a protective sleeve arrangement arranged around the distal part of the urinary catheter, a proximal end of the protective sleeve arrangement being releasably connected to the first compartment, e.g. to an annular recession encircling the opening, at or in the vicinity of said opening, and a distal end of the protective sleeve arrangement being connected to the urinary catheter, at or in the vicinity of a distal end thereof, wherein the protective sleeve arrangement comprises at least two sleeves being telescopically displaceable in relation to each other, wherein the protective sleeve arrangement is transformable between a retracted position and an extended position. The method further includes pulling said catheter out from said protective sleeve arrangement, and upon continued pulling, pulling said sleeves apart, thereby expanding the protective sleeve arrangement into its extended position. The method also includes releasing the protective sleeve arrangement from the package, thereby releasing the catheter from the package, whereby the extended protective sleeve arrangement forms a protective cover over at least a part of the length of tubular shaft of the catheter.

These and other aspects of the disclosed technology will be apparent from and elucidated with reference to the embodiments described hereinafter.

BRIEF DESCRIPTION OF THE DRAWINGS

For exemplifying purposes, the disclosed embodiments will be described in closer detail in the following with reference to embodiments thereof illustrated in the attached drawings, wherein.

DETAILED DESCRIPTION OF PREFERRED EMBODIMENTS

In the following detailed description preferred embodiments of the invention embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g., the length of the medical device, etc.

Individuals who suffer from urinary incontinence will normally self-catheterize several times a day. Self-catheterization involves removing the catheter assembly from its package and inserting and advancing the catheter tube through the user's urethra. However, preparation and manipulation of known catheter assemblies is often complicated and tedious. Further, often users of intermittent urinary catheters have limited or diminished dexterity, e.g., as a result of spinal cord injuries. Also, users of intermittent catheters are often required to self-catheterize outside the privacy of the home, such as in public restrooms. Thus, for these and other reasons, it is desirable that the intermittent catheters are provided in discrete packaging that is easy to open and manipulate, which are compact and portable, and wherein the catheter can be deployed and used in a way that alleviates concerns about inadvertent urine leakage or spillage and avoids pain or discomfort to the user.

In particular, male catheters are relatively long, making the catheter assemblies large and difficult to handle.

Thus, there is still a need for improved urinary catheter assemblies, and in particular male urinary catheter assemblies. The assembly should preferably be relatively simple and cost-efficient to produce. Further, the assembly should be easy and intuitive to open and use, even for users with reduced dexterity. The assembly should also preferably be rather small, so that it can easily be carried around by the user in his/her daily life. Further, the product should preferably enable performing of the catheterization without contamination of at least the insertable parts of the product. Thus, there is a general need for a more simplified catheterization procedure, and for a urinary catheter assembly enabling this. It is therefore an object of the disclosed embodiments to provide a urinary catheter assembly which at least alleviates the above-discussed problems.

Figure 1:
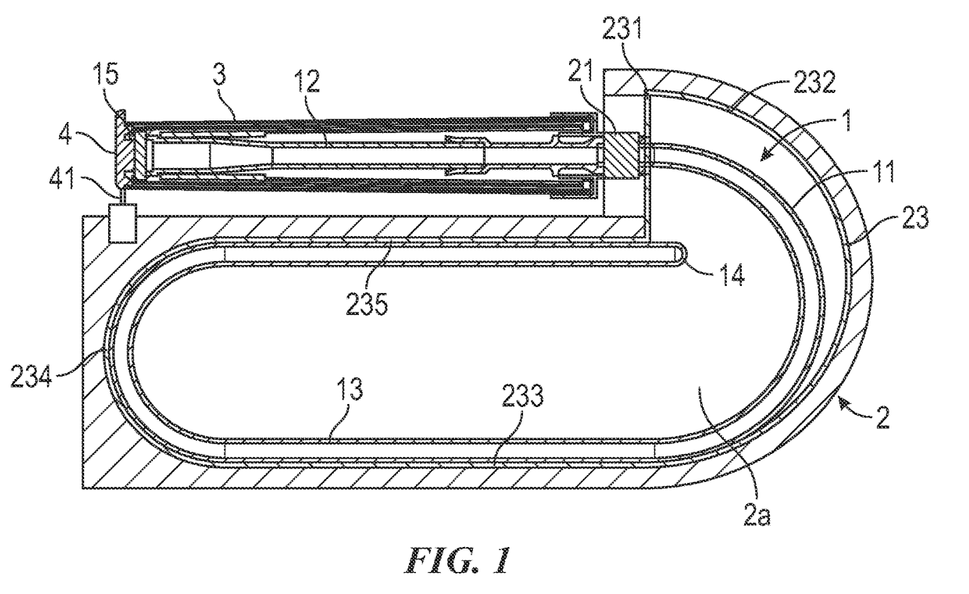
FIG. 1 is a cross-sectional view of a urinary catheter assembly in accordance with one embodiment of the disclosed embodiments.
Figure 2:
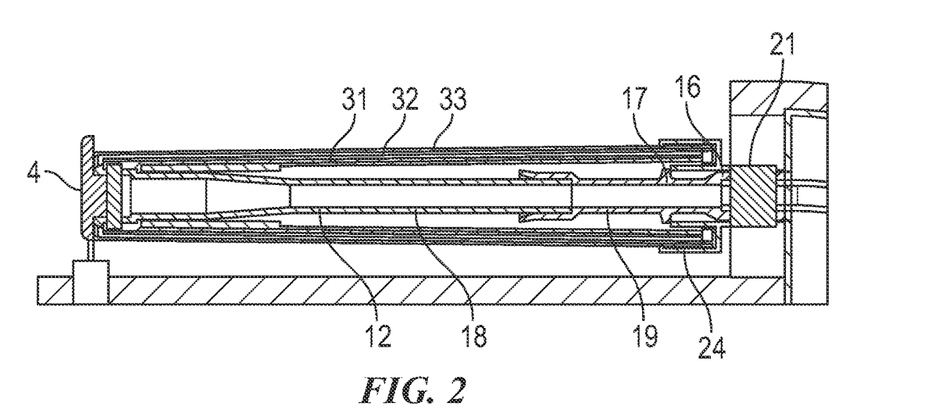
FIG. 2 is a more detailed view of a part of the urinary catheter assembly in FIG. 1.

A urinary catheter assembly as illustrated in FIGS. 1 and 2 comprises a catheter 1 having an insertable section 11, comprising an insertable, proximal part, with an insertion tip, and a catheter shaft, and a non-insertable section 12, a distal part, forming a connector part. The non-insertable section 12 has a larger diameter than the insertable section 11 at least on a part thereof. The rear end of the non-insertable section may be flared or funnel-shaped, and may be arranged to be connected to a tapered connection part of a urine collection bag or the like. However, the non-insertable section may alternatively have a relatively uniform cross-sectional area. The catheter is accommodated in a first compartment 2a of a package 2, forming a closed cavity in which the catheter is arranged. The package may optionally be arranged in an outer container, such as a bag or pouch.

At least a part of the insertable section 11 forms an insertable length to be inserted through a urethra of the user.

The insertable section comprises a tubular shaft 13 and an insertion tip 14, which may be a closed, rounded end. Further the insertable section may comprise inlet openings (not shown), arranged in the vicinity of the insertion tip, so called catheter eyes or eyelets, leading into a lumen extending through the catheter, and into a discharge outlet or drainage opening 15 arranged at the rearward end of the non-insertable section.

The insertable section may be 80-140 mm for a female user and 200-350 mm for a male user. The urinary catheter assembly is in particular suitable for male catheters.

The insertable section 11 may comprise a hydrophilic surface, and form a hydrophilic catheter, as is per se well known in the art. The hydrophilic surface may be in the form of a hydrophilic surface coating, for example polyvinylpyrrolidone (PVP), and which provides a low-friction surface when wetted with a wetting fluid. Even though PVP is the preferred hydrophilic material, other hydrophilic materials may be used, such as polyethylene oxide, polyvinyl alcohol, and the like. However, instead of a hydrophilic surface coating, the entire insertable section of the catheter may be formed of a hydrophilic material.

In case a hydrophilic catheter is used, the urinary catheter assembly may also comprise a wetting fluid. However, the wetting fluid for activation of the catheter need not be provided within the package/first compartment. Instead, a wetting fluid may be poured into the package/first compartment after opening of the package/first compartment, for wetting of the catheter while it still remains in the package/first compartment. In some occasions, the catheter may even be removed from the package/first compartment and wetted e.g. in a different container, even though this is normally not preferred.

However, preferably the wetting fluid is arranged within the assembly, and preferably within the package/first compartment, so that the hydrophilic surface of the catheter can be activated even before opening of the package/first compartment. In one embodiment, the wetting fluid is arranged separated from the catheter, in a wetting fluid container (not shown), such as a pouch or a sachet, or in a separate wetting fluid compartment of the package. The wetting fluid container or compartment can be openable by means of e.g., exerting a pressure to the container or compartment, whereby the wetting fluid is released into the package/first compartment, thereby wetting the hydrophilic surface of the catheter. The wetting fluid container or compartment may also be arranged to open automatically when the catheter assembly is opened, when extraction of the catheter from the package/first compartment is initiated. The wetting fluid may alternatively be arranged in a wetting fluid compartment encircling a part of the catheter shaft, and preferably a distal part, not provided with the hydrophilic coating, so that wetting of the hydrophilic coating is obtained while the catheter shaft is pulled out through the wetting fluid compartment.

In another embodiment, the wetting fluid is arranged directly in the first compartment of the package accommodating the catheter, so that the hydrophilic surface of the catheter is in direct contact with the wetting fluid during storage, and thereby is maintained in an activated, ready-to-use state.

The wetting fluid is preferably a liquid, and most preferably an aqueous liquid, such as water or saline. However, the wetting fluid may also be a gas, providing a moist atmosphere in the package/first compartment sufficient for activation of the hydrophilic surface. Thus, the wetting fluid may be any fluid, gas or liquid, that wets/activates a hydrophilic surface of the catheter.

However, alternatively the catheter may be non-hydrophilic, and may e.g., be lubricated with gel prior to insertion.

In case a non-hydrophilic catheter is used, the urinary catheter assembly may comprise a supply of lubricant, such as a compartment arranged overlying the catheter shaft, so that the shaft is lubricated while being pulled out from the tubular case.

The first compartment 2a is provided with an opening 21. The first compartment is arranged to enclose the proximal part, and at least a part of the tubular shaft therein, and preferably at least the entire insertable section 11. However, at least the distal, non-insertable part 12 of the urinary catheter forms an extending part extending out from the first compartment through the opening.

In one embodiment, an enlarged part 16 may be provided in the proximal end of the non-insertable part 12. This enlarged part preferably has a larger outer diameter than the catheter shaft, and preferably has an outer diameter essentially corresponding to an inner diameter of the opening 21. This enlarged part 16 may be inserted into the opening when in the storage position, and thereby releasably connected to the opening 21 and the first compartment 2a. The connection may be formed by a friction fit, but additional connection elements may also be used, such as an adhesive, welding or the like. The connection preferably forms a seal between the catheter and the package/first compartment.

The non-insertable part 12 may further comprise a second enlarged part 17, arranged distally from the first enlarged part 16. The second enlarged part 17 has, at least at some positions, a greater diameter than the first enlarged part 16. Hereby, the second enlarged part extends laterally outwards from the first enlarged part. The second enlarged part 17 preferably has greater lateral dimensions than the opening 21. The second enlarged part 17 may e.g., be disc shaped, and forma flange on the non-insertable part 12. The second enlarged part 17 forms a stop, preventing the catheter from being moved further into the first compartment 2a. In the storage position, the second enlarged part 17 may be in abutment with the rim of the opening 21.

The distal section 18 of the non-insertable part 12, which comprises the drainage opening 15 at the distal end, and which may e.g., be flared and generally funnel shaped, may be formed as an integral, monolithic element together with the proximal section 19 of the non-insertable part 12, comprising the first enlarged part 16 and the second enlarged part 17. However, the distal section 18 and the proximal section 19 may also be made as separate parts. These parts are then preferably non-releasably connected to each other, e.g., by means of an adhesive, welding or the like.

The opening 21 of the first compartment is preferably arranged as a short tube of relatively rigid material, and which is integrally formed in, or otherwise attached to, the rest of the package/first compartment.

The first compartment 2a is arranged to enclose the insertable part 11 of the catheter. The first compartment may also be arranged of a relatively rigid material. However, preferably the first compartment is made of a flexible material. In one embodiment, the first compartment 2a of the package 2 may be formed of a sheet material, such as a foil. The package/first compartment is preferably capable of maintaining the interior in a sterile state. Further, the package/first compartment is preferably liquid impermeable, and most preferably made of a gas impermeable material. For example, the material may be a laminate, comprising a layer of a gas and/or liquid barrier material, such as $SiO_x$, $AlO_x$ or a metal layer, i.e., a metallized laminate. However, somewhat impermeable materials may also be used, in particular for assemblies where the package is arranged in an outer container.

The first compartment 2a is arranged to maintain the urinary catheter, when arranged in the package/first compartment, in a state during storage. To this end, the container may have curved inner boundaries 23, forming a border which the catheter can follow, and thereby be maintained in the curled/curved state. When the first compartment is formed by a sheet material, these boundaries may e.g., be formed by welding, or alternatively by use of an adhesive or the like. However, boundaries having a similar curvature may also be obtained in other types of containers, such as in a tubular container made of a more rigid material. In such a case, the tube may be arranged to follow the same path as the one intended for the catheter, such as being arranged in a shape resembling a U, a C, or the like. However, other bent, folded or otherwise curved shapes are also feasible.

In the illustrative embodiment of FIG. 1, the first compartment 2a is made of a sheet material. The first compartment may be formed by two sheets being connected around the edges, or by a folded sheet, being connected together around the edges not formed by the fold. Here, the inner boundary 23 of the first compartment contains, as seen from the opening 21, a first straight part 231, then a curved part 232, generally forming a semicircle, a second straight part 233, leading past the opening 21, a second curved part 234, also generally forming a semicircle, but with a slightly smaller diameter than the first curved part, and finally a straight part 235 leading back to the opening 21.

However, alternatively, the first compartment may be formed by a tube or the like, or partly comprise such a tube.

In this embodiment, the catheter is curled into about 1.5 turns, i.e., with a full and a half convolution. This generally reduces the length of the catheter to a third of its original length, allowing the catheter assembly to be correspondingly compacted.

In the illustrative embodiment, the cavity holding the catheter is open in the center, and only defined by the outer boundaries. However, additional boundaries, e.g., formed by welds, may also be formed in the interior of the cavity. Such additional boundaries may e.g., be used to define channels extending along the intended curved/curled path of the catheter.

For example, in the illustrated example, the free area inside the curled catheter may comprise an additional inner boundary, e.g., defining a circle or ellipse, thereby reducing the space of the cavity.

The catheter may also be arranged to be more or less curved/curled. For example, the catheter may be arranged in less than a full convolution, such as generally forming the shape of a C or U. Alternatively, the catheter may be arranged in more than 1 or 1.5 convolutions, such as in about 2 or about three convolutions.

For embodiment where the catheter extends over more than 1.5 convolutions, the same container/first compartment as shown in FIG. 1 may still be used. Hereby, the catheter will at places overlap itself, and at least parts of the convolutions will be in touch with each other. However, for such embodiments having more convolutions, the boundaries may be used to define also the additional convolutions.

Figure 4:
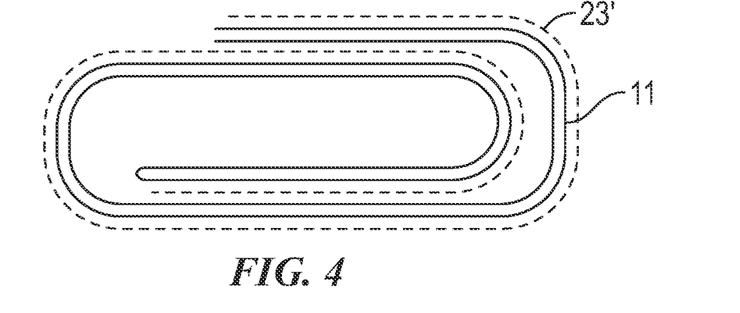
FIG. 4 is a schematic illustration of a package arranged to maintain the catheter in a curled or curved state, in accordance with another embodiment.
Figure 5:
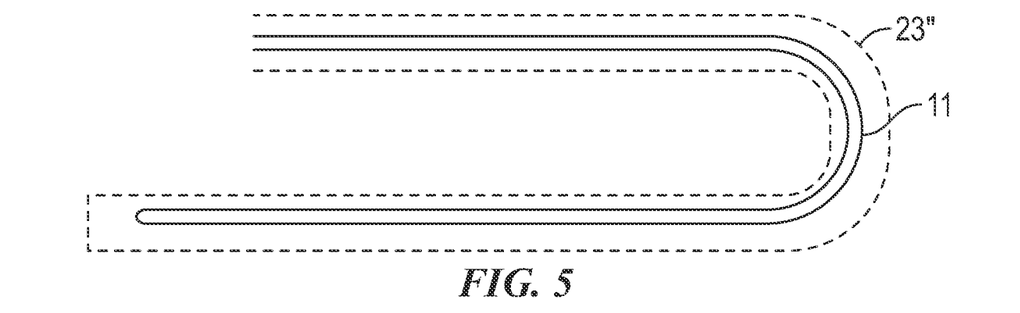
FIG. 5 is a schematic illustration of another embodiment of a package arranged to maintain the catheter in a curled or curved state.

In FIG. 4, a schematic illustration is provided of an alternative embodiment, in which the insertable part 11 of the catheter is arranged in about two convolutions, where the second convolution extends inside the first convolution. Here, the boundary 23' is arranged in a helix configuration, forming the paths for the catheter. In another example, as schematically illustrated in FIG. 5, the catheter is arranged in less than a full convolution, with a shape resembling a U. Here, boundaries 23" are provided on both sides of the catheter path, defining a channel for receiving the insertable part 11 of the catheter. Such boundaries may also be realized by welds in a container formed by sheet materials. However, as will be readily appreciated by the skilled reader, such channels may also be realized e.g., by a tubular container, made by a more rigid material.

The above shown curved or curled shape of the catheter are merely exemplary, and many other ways of forming a compact shaped catheter are feasible, and may defined by different types of boundaries within the container/first compartment. However, it is generally preferred to have curves with a relatively large radius of curvature, thereby avoiding kinking of the catheter shaft, and also to reduce the permanent deformation of the catheter due to the memory effect of the catheter shaft material.

The urinary catheter assembly further comprises a protective sleeve arrangement 3 arranged around the extending part of the urinary catheter, i.e., the non-insertable part 12. The protective sleeve arrangement functions as an insertion aid, facilitating manipulation of the catheter for insertion into the urethra. In addition, the protective sleeve arrangement provides protection for the catheter shaft against contamination, and enables manipulation of the catheter without touching it. Still further, the protective sleeve arrangement provides a reinforcement for the catheter, thereby avoiding kinking and deformation of the catheter, and also ensures that the catheter is relatively straight, despite any memory effect in the catheter shaft.

The protective sleeve arrangement 3 comprises a plurality of sleeves. In the illustrative example, the protective sleeve arrangement comprises three sleeves, but it is also feasible to use only two sleeves, or to use four or more sleeves. The sleeves are telescopically displaceable in relation to each other, and are in a compacted storage state arranged essentially overlying each other. The length of the protective sleeve arrangement in this state essentially corresponds to the length of the longest sleeve. In an expanded, extended position, the sleeves are telescopically displaced in relation to each other. In this extended state, the length of the protective sleeve arrangement generally corresponds to the sum of the lengths of the sleeves, apart from the small overlap areas formed between the sleeves.

In the illustrative embodiment, the protective sleeve arrangement comprises an inner sleeve 31, an intermediate sleeve 32 and an outer sleeve 33. The sleeves may be of generally the same length. The length of each sleeve may e.g., be in the range of 6-10 cm.

The outer sleeve 33, having the greatest diameter, may have its proximal end releasably connected to the package/first compartment. To this end, the opening 21 of the first compartment 2a may be provided with an annular recession 24 encircling the opening tube. The annular recession may e.g., be formed in a flange surrounding the tube. The annular recession may be arranged to receive and connect to the protective sleeve arrangement when in the retracted position, and in particular to the outer sleeve 33.

The inner sleeve 31, i.e., the sleeve having the smallest diameter, preferably has a distal end connected to the non-insertable part 12 of the urinary catheter, and preferably at, or in the vicinity of, the drainage opening 15. This connection may also be releasable.

The protective sleeve arrangement 3, in its extended position preferably has the sleeve with the smallest diameter, i.e., the inner sleeve 31, arranged closest to the distal end of the catheter, the sleeve with the largest diameter, i.e., the outer sleeve 33, arranged closest to the proximal end of the catheter, and the intermediate sleeve 32 therebetween.

The protective sleeve arrangement is preferably relatively rigid, so that it cannot be easily compressed or the like. The rigidity of the protective sleeve arrangement is preferably such that it cannot be bent during ordinary handling of the catheter. It is further preferably such that the protective sleeve arrangement cannot be compressed onto the catheter by moderate, or even high, finger pressure during handling. Preferably, the at sleeves of the protective sleeve arrangement each has a rigidity which is greater than the rigidity of the tubular shaft of the urinary catheter.

The inner sleeve 31 is preferably releasably connected to non-insertable part 12 of the urinary catheter, and the distal part of the urinary catheter is preferably arranged telescopically displaceable in the protective sleeve arrangement. Hereby, the non-insertable part 12 of the urinary catheter may be telescoped out from the inner sleeve 31 during extraction of the catheter from the package/first compartment, so that the protective sleeve arrangement then primarily covers the insertable part of the catheter when in the extended state.

During such telescoping, at least one of the enlarged part 16 and the enlarged part 17, forming outwardly protruding parts, may be arranged to interact with an inwardly protruding part 311 of the inner sleeve, arranged at, or in the vicinity of, the distal end of the inner sleeve 31. This inwardly protruding part 311 may be formed as a section with smaller cross-sectional diameter, such as an inwardly protruding flange. Hereby, the distal part of the catheter will be brought into engagement with the inner sleeve, upon contact between the inwardly protruding part and the outwardly protruding part, thereby forming a connection between the distal part of the catheter and the inner sleeve. This prohibits complete extraction of the distal part from the inner sleeve, and brings the inner sleeve away from the package/first compartment together with the catheter upon continued extraction.

Further, the inner sleeve 31 may comprise an outward protrusion 312 at, or in the vicinity of, a proximal end thereof, e.g., formed as a section with enlarged cross-sectional diameter, such as an outwardly protruding flange, arranged to engage with an inward protrusion 321 at, or in the vicinity of, the distal end of the intermediate sleeve 32. The inward protrusion 321 may in a similar way be arranged as a section with a smaller cross-sectional diameter, such as inwardly protruding flange.

In analogy, the intermediate sleeve 32 may comprise an outward protrusion 322 at, or in the vicinity of, a proximal end thereof, e.g., formed as a section with enlarged cross-sectional diameter, such as an outwardly protruding flange, arranged to engage with an inward protrusion 331 at, or in the vicinity of, the distal end of the outer sleeve 33. The inward protrusion 331 may in a similar way be arranged as a section with a smaller cross-sectional diameter, such as inwardly protruding flange.

Hereby, each inner sleeve will be brought into engagement with its closest outer sleeve, upon contact between the inward protrusion and the outward protrusion, thereby forming a connection between the sleeves. This prohibits complete extraction of any sleeve from its adjacent outer sleeve, and brings the sleeves sequentially away from the package/first compartment together with the catheter upon continued extraction, as the protective sleeve arrangement gradually assumes its extended state.

The outward protrusions, or the outwardly protruding parts, may be provided as a narrowing section, providing a decreased internal diameter compared to at least an adjacent part, and the inward protrusions, or the inwardly protruding parts, may be provided as an expanded section, providing an enlarged external diameter compared to at least an adjacent part. The narrowing sections and the expanded sections may form a stop abutment when brought together.

The sleeves are preferably formed by solid walls around their entire circumference, and along their entire lengths. The sleeves may e.g., be made of poly propene (PP), poly ethylene (PE), Sulpac®, or the like. The protective sleeve arrangement can e.g., be produced by injection molding and/or extrusion.

The urinary catheter assembly may further comprise a removable or openable closure 4 arranged over the drainage opening 15 in a distal end of the urinary catheter. The closure may e.g., comprise a cap or lid arranged to close the drainage opening of the catheter, and which may in a closed state be partly inserted into the drainage opening 15. The cap or lid may further be connected to the catheter by a hinge 41 or the like, so that it remains in place even after being opened. In this case, the cap or lid may also be used as a grip to initiate extraction of the catheter out from the package/first compartment. The cap or lid may also be connected to the package.

With the closure 4 sealing the drainage opening 15, a sealed compartment may be formed by the first compartment 2a, the sealed connection between the non-insertable part 12 of the catheter formed by the enlarged part 16 in the opening 21, and the closure 4. This sealed compartment may be arranged to maintain the insertable part of the catheter sterile, and may also be arranged to maintain the wetting liquid within the sealed compartment. In some embodiments, the exterior of the rearward part and the protective sleeve arrangement are not maintained in a sterile state. However, in other embodiments, the interior of the second compartment 2b may also be sterile, in order to maintain the rearward part and the protective sleeve arrangement in a sterile state.

The lid or cap may be connected to the drainage opening by a friction fit. However, it may also be connected by other means, such as by a screw connection. It is also possible to use other types of closures, such as a peel-off membrane, a flip-open cap or the like. Alternatively, or additionally, the second compartment 2b may have an opening, such as a tear opening, a peel opening or the like.

Figure 3A:
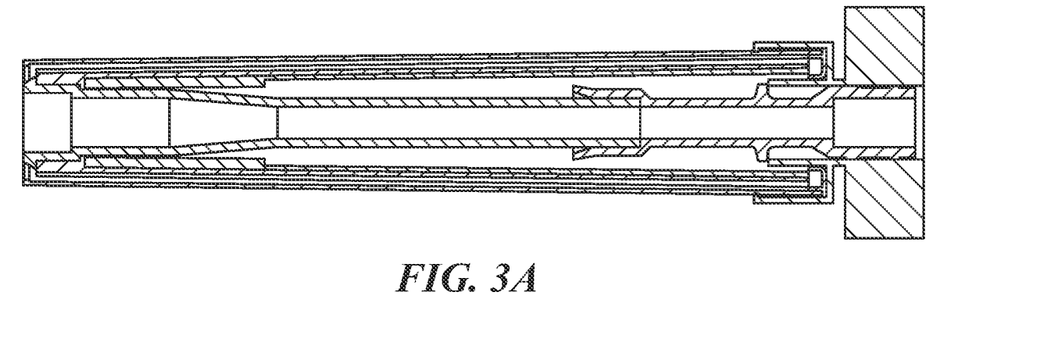
FIGS. 3a-e are cross-sectional views of the urinary catheter assembly in FIG. 1 during various steps of extraction of the catheter.

In the storage state, the protective sleeve arrangement is in a retracted, compacted state, and covers only a very limited part of the catheter, such as the connector or the non-insertable part of the catheter. Such a state is illustrated in FIGS. 1, 2 and 3a. The remainder of the catheter, including the insertable part of the catheter shaft, resides in the first compartment of the package. During extraction of the catheter from the package/first compartment, the protective sleeve arrangement is extended into its extended state, and is released from the package/first compartment.

Figure 3B:
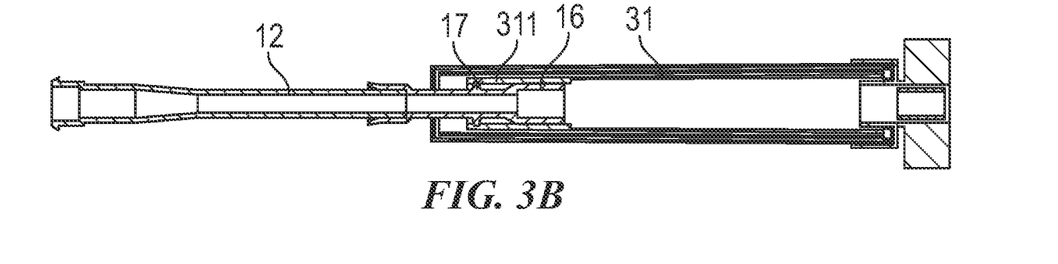

Upon use, the user pulls the rear, distal, end of the catheter away from the package/first compartment, for example by gripping the cap, or directly gripping the distal part of the catheter. This releases the connection between the catheter and the inner sleeve 31. Then, the catheter, and its non-insertable part 12, is telescopically displaced within the protective sleeve arrangement 3. After a while, one or both of the enlarged parts 16 and 17 close to or at the proximal end of the non-insertable part 12 will come into engagement with the inward protrusion 311 of the inner sleeve. This intermediate state is illustrated in FIG. 3b.

Figure 3C:
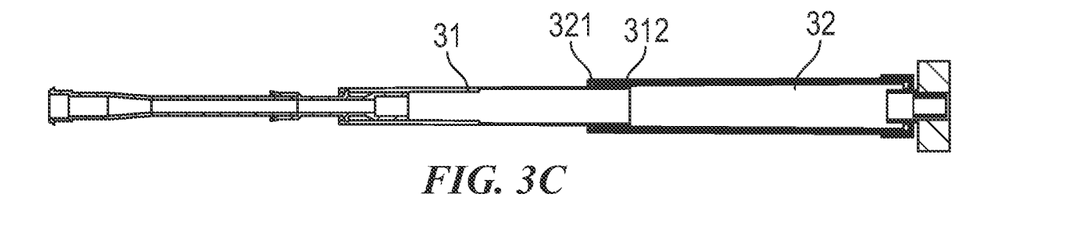

As the catheter is continued to be pulled out the non-insertable part 12 hereby brings the inner sleeve 31 along, and telescopically displaces it through the intermediate sleeve 32. After a while, the outward protrusion 312 of the inner sleeve, arranged at or close to the proximal part will come into engagement with the distally arranged inward protrusion 321 of the intermediate sleeve. This intermediate state is illustrated in FIG. 3c.

Figure 3D:
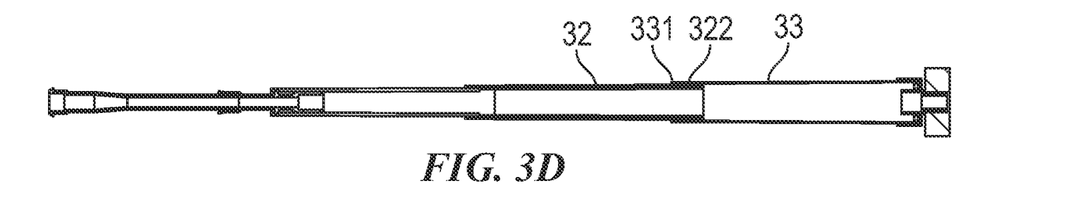

As the catheter is continued to be pulled out the now extended non-insertable part 12 and inner sleeve 31 brings the intermediate sleeve 32 along, and telescopically displaces it through the outer sleeve 33. After a while, the outward protrusion 322 of the inner sleeve, arranged at or close to the proximal part will come into engagement with the distally arranged inward protrusion 331 of the outer sleeve. This intermediate state is illustrated in FIG. 3d.

Figure 3E:
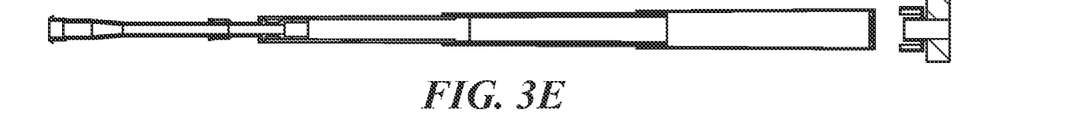

As the catheter is continued to be pulled out, away from the package/first compartment, this will then release the releasable connection between the protective sleeve arrangement 3 and the package 2/first compartment 2a, and is illustrated in FIG. 3e.

In this state, the protective sleeve arrangement is fully extended, and covers a substantial part of the insertable part 11 of the catheter. However, at least a small part of the catheter shaft preferably extends out from the extended protective sleeve 3 arrangement after extraction of the catheter from the package/first compartment. In this position, the user may use the extended protective sleeve arrangement as a handle, and grip it for clean manipulation and insertion of the catheter into the urethra. Due to the significant length of the protective sleeve arrangement, it is easy and convenient to grip. Further, the catheter shaft is maintained in a relatively straight state by the protective sleeve arrangement, thereby facilitating insertion of the catheter. Since only the protective sleeve arrangement need to be touched, the risk of contaminating the catheter during this procedure is greatly alleviated.

As the catheter is inserted into the urethra, the protective sleeve arrangement may again be compacted into its retracted state, thereby allowing the entire insertable length of the catheter shaft to be inserted. The compaction of the protective sleeve arrangement may here be obtained by manually moving the telescopic sleeves of the protective sleeve arrangement together, or automatically, by simply pulling the proximal end of the protective sleeve arrangement to the glans of the penis during insertion.

After use, when the catheter is expelled from the urethra, the protective sleeve arrangement may again, optionally, be enlarged, into its extended state, to facilitate handling of the catheter in a clean manner during subsequent activities, such as cleaning of the catheter, discarding of the catheter, or rearrangement of the catheter into the package/first compartment.

In the embodiment discussed in relation to FIG. 1, the package comprises only one compartment, the first compartment 2a, in which the proximal part of the catheter is enclosed. The distal part of the catheter hereby extends out from the package. A sterile environment for the proximal part of the catheter is here formed by the package 2/first compartment 2a, the protective sleeve arrangement 3 and the closure 4.

However, in other embodiments, the package may also comprise further compartments, e.g., enclosing also the distal part of the catheter. Such embodiments will now be discussed in relation to FIGS. 6 and 7.

Figure 6:
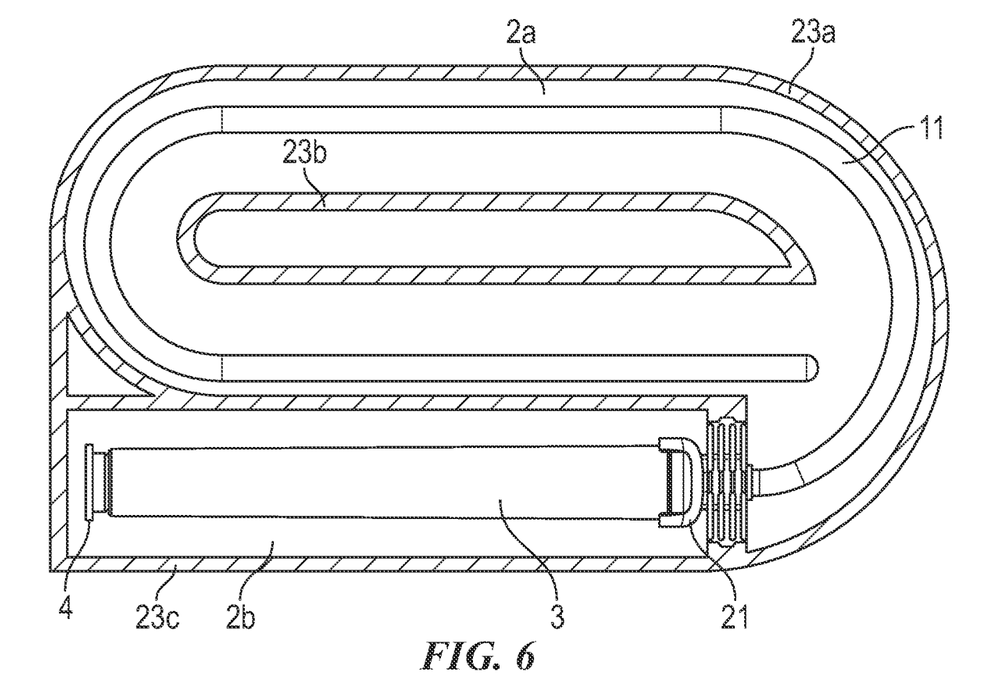
FIG. 6 is a to view of a urinary catheter assembly in accordance with another embodiment of the present invention.

In the embodiment of FIG. 6, the first compartment 2a may be formed and arranged essentially as in the first discussed embodiment. The first compartment 2a here has an inner boundary 23a, formed e.g., by a weld, forming the curved or curled shape of the catheter shaft 11 maintained during storage. In addition, the first compartment may comprise an additional boundary 23b, arranged inside the boundary 23a, and with a distance from the inner boundary 23a. The two boundaries 23a and 23b hereby form a channel in which the catheter shaft 11 is received. However, the arrangement of the first compartment 2a as shown in FIG. 1 may also be used.

Further, the package also comprises a second compartment 2b, adjacent the first compartment 2a, such that the opening 21 connects the first and second compartments, forming a passage between the compartments. The second compartment is arranged to enclose the distal part of the catheter, extending out from the first compartment, and the protective sleeve arrangement 3. The second compartment may e.g., be formed by a third weld 23c. The third weld 23c may e.g., be arranged as an extension of the inner boundary/weld 23 a forming the first compartment.

In this embodiment, the distal part of the catheter, together with the protective sleeve arrangement 3, may be maintained in a sterile state in the second compartment 2b, and the proximal part of the catheter may be maintained in a sterile state in the first compartment. In this embodiment, the opening 21 need not be closed, since both compartments may be sterile. However, the opening 21 may still be closed, e.g., in order to maintain the wetting fluid in the first compartment 2a, and avoid that the wetting fluid spreads into the second compartment 2b. To this end, a closure 4 may also be provided at the distal end of the catheter.

In use, the user may here first open the second compartment 2b, and thereby get access to the distal part of the catheter. To this end, the second compartment may be provided with a tear opening, a peel-opening or the like. The catheter may thereafter be removed from the first compartment 2a in the same way as discussed in relation to the first embodiment.

Figure 7:
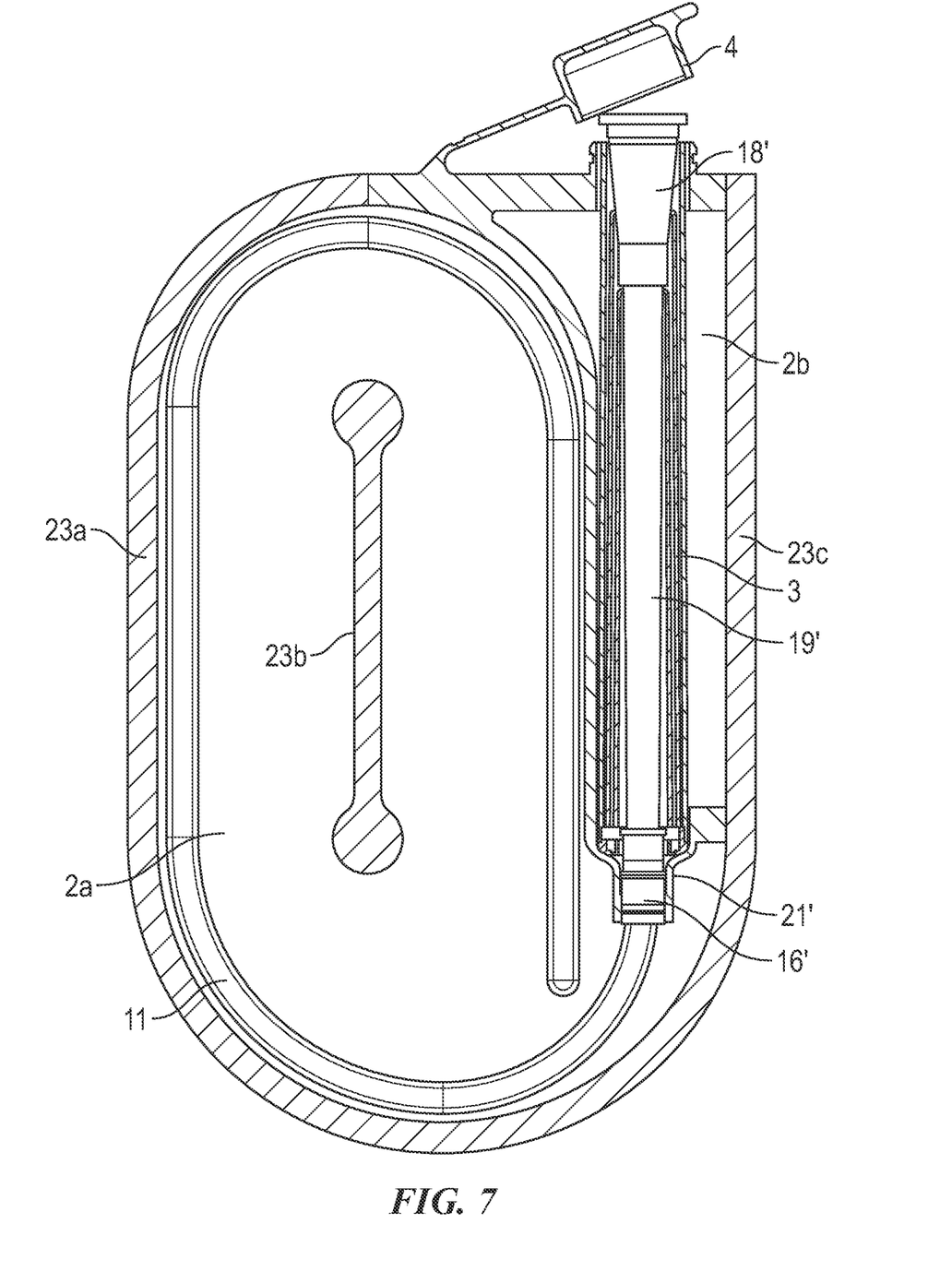
FIG. 7 is a view, partly in cross-section, of a urinary catheter assembly in accordance with another embodiment of the present invention.

In the embodiment of FIG. 7, the first compartment 2a may also be formed and arranged essentially as in the first discussed embodiment. The first compartment 2a here has an inner boundary 23a, formed e.g., by a weld, forming the curved or curled shape of the catheter shaft 11 maintained during storage. In addition, the first compartment may comprise an additional boundary 23b, arranged inside the boundary 23a, and with a distance from the inner boundary 23a. The two boundaries 23a and 23b hereby form a channel in which the catheter shaft 11 is received. However, the arrangement of the first compartment 2a as shown in FIG. 1 may also be used.

Further, the package also comprises a second compartment 2b, adjacent the first compartment 2a, such that the opening 21' connects the first and second compartments, forming a passage between the compartments. The second compartment is arranged to enclose the distal part of the catheter, extending out from the first compartment, and the protective sleeve arrangement 3. The second compartment may e.g., be formed by a third weld 23c. The third weld 23c may e.g., be arranged as an extension of the inner boundary/weld 23a forming the first compartment.

In this embodiment, the distal part of the catheter, together with the protective sleeve arrangement 3, may be maintained in a sterile state in the second compartment 2b, and the proximal part of the catheter may be maintained in a sterile state in the first compartment. In this embodiment, the opening 21' need not be closed, since both compartments may be sterile. However, the opening 21' may still be closed, e.g., in order to maintain the wetting fluid in the first compartment 2a, and avoid that the wetting fluid spreads into the second compartment 2b. To this end, a closure 4 may also be provided at the distal end of the catheter. In the embodiment of FIG. 7, this closure 4 also serves as a closure of an opening of the second compartment 2b.

In the embodiment of FIG. 7, the non-insertable part of the catheter may comprise a distal section 18', forming e.g., a flared end, and an oppositely arranged enlarged part 16', having a diameter greater than the diameter of the shaft of the catheter. Here, the enlarged part 16' may form a friction fit, or otherwise be connected to, the opening 21'. A tubular part 19' may be arranged between the distal section 18' and the enlarged part 16'.

In use, the user may here open closure 4, thereby opening the second compartment 2b, and also get access to the distal part of the catheter. The catheter may thereafter be removed from the first compartment 2a in the same way as discussed in relation to the previously discussed embodiments.

Specific embodiments of the invention have now been described. However, several alternatives are possible, as would be apparent for someone skilled in the art. For example, although the wetting fluid in the described embodiments is arranged in direct contact with the catheter, it may alternatively be arranged separated from the catheter, in a wetting fluid container. Further, more than three sleeves may be used in the protective sleeve arrangement, as well as only two. Still further, the arrangement of the catheter in a curved or curled state may be realized in many different ways.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A urinary catheter assembly, comprising:
    a urinary catheter having a proximal part with an insertion tip, a distal part and a tubular shaft extending there between, wherein the distal part, on at least a part thereof, has a greater cross-sectional dimension than the tubular shaft and the proximal part;
    a package having at least a first compartment with an opening, said first compartment being arranged to enclose the proximal part and at least a part of the tubular shaft therein, and wherein the part of the urinary catheter arranged in the first compartment is arranged in a curved or curled state during storage; and
    a protective sleeve arrangement arranged around the distal part of the urinary catheter, a distal end of the protective sleeve arrangement being connected to the urinary catheter, at or in the vicinity of a distal end thereof;
    wherein the protective sleeve arrangement comprises at least two sleeves being telescopically displaceable in relation to each other, and wherein the protective sleeve arrangement is transformable between a retracted position and an extended position, the protective sleeve arrangement in the extended position being arranged to form a protective cover over at least a part of the length of the tubular shaft of the catheter.

2. The urinary catheter assembly of claim 1, wherein at least the distal part of the urinary catheter forms an extending part extending out from the first compartment through said opening.

3. The urinary catheter assembly of claim 2, wherein a proximal end of the protective sleeve arrangement is releasably connected to the package, at or in the vicinity of said opening.

4. The urinary catheter assembly of claim 1, wherein the package comprises sheet material.

5. The urinary catheter assembly of claim 1, wherein the first compartment comprises a gas or liquid impermeable material.

6. The urinary catheter assembly of claim 1, wherein the urinary catheter is a hydrophilic urinary catheter, and wherein the assembly further comprises a wetting fluid for activation of the hydrophilic urinary catheter.

7. The urinary catheter assembly of claim 1, wherein the protective sleeve arrangement comprises at least three sleeves being telescopically displaceable in relation to each other.

8. The urinary catheter assembly of claim 1, wherein a sleeve of said at least two sleeves having a smaller smallest diameter has an end connected to the urinary catheter.

9. The urinary catheter assembly of claim 1, wherein each of the at least two sleeves of said protective sleeve arrangement has a rigidity which is greater than rigidity of the tubular shaft of the urinary catheter.

10. The urinary catheter assembly of claim 1, wherein the protective sleeve arrangement is releasably connected to the urinary catheter, and wherein the distal part of the urinary catheter is arranged telescopically displaceable in relation to the protective sleeve arrangement.

11. The urinary catheter assembly of claim 10, wherein the distal part, at a proximal part thereof, is provided with an outwardly protruding part, arranged to engage with an inwardly protruding part of an inner sleeve of said at least two sleeves.

12. The urinary catheter assembly of claim 1, wherein the package is provided with an annular recession encircling said opening, said annular recession arranged to receive and connect to the protective sleeve arrangement when in the retracted position.

13. The urinary catheter assembly of claim 1, further comprising a removable or openable closure arranged over a drainage opening in a distal end of the urinary catheter, the closure together with the protective sleeve arrangement and the first compartment forming a closed interior space for the catheter, said closed interior space forming a sterile and moisture proof compartment.

14. The urinary catheter assembly of claim 1, wherein the at least two sleeves are arranged essentially entirely overlying each other in the retracted position.

15. The urinary catheter assembly of claim 1, wherein the protective sleeve arrangement, in its extended position, has the sleeve with the smallest diameter arranged closest to an end of the distal part of the urinary catheter, and the sleeve with the largest diameter arranged closest to an end of the proximal part of the urinary catheter.

16. The urinary catheter assembly of claim 1, wherein every sleeve being arranged outwardly of any other of the at least two sleeves comprises an inward protrusion at or in the vicinity of a distal end, and wherein every sleeve being arranged inwardly of any other of the at least two sleeves comprises an outward protrusion at or in the vicinity of a proximal end.

17. A urinary catheter assembly, comprising:
a urinary catheter having a proximal part with an insertion tip, a distal part and a tubular shaft extending there between, wherein the distal part, on at least a part thereof, has a greater cross-sectional dimension than the tubular shaft and the proximal part;
a package having at least a first compartment with an opening, said first compartment being arranged to enclose the proximal part and at least a part of the tubular shaft therein, and wherein the part of the urinary catheter arranged in the first compartment is arranged in a curved or curled state during storage; and
a protective sleeve arrangement arranged around the distal part of the urinary catheter, a distal end of the protective sleeve arrangement being connected to the urinary catheter, at or in the vicinity of a distal end thereof;
wherein the protective sleeve arrangement comprises at least two sleeves being telescopically displaceable in relation to each other and wherein the protective sleeve arrangement is transformable between a retracted position and an extended position,
wherein the protective sleeve arrangement, in its extended position, has a sleeve with a smaller diameter arranged closest to an end of the distal part of the urinary catheter, and a sleeve with a larger diameter arranged closest to an end of the proximal part of the urinary catheter.

18. A urinary catheter assembly, comprising:
a urinary catheter having a proximal part with an insertion tip, a distal part and a tubular shaft extending there between, wherein the distal part, on at least a part thereof, has a greater cross-sectional dimension than the tubular shaft and the proximal part;
a package having at least a first compartment with an opening, said first compartment being arranged to enclose the proximal part and at least a part of the tubular shaft therein, and wherein the part of the urinary catheter arranged in the first compartment is arranged in a curved or curled state during storage; and
a protective sleeve arrangement arranged around the distal part of the urinary catheter, a distal end of the protective sleeve arrangement being connected to the urinary catheter, at or in the vicinity of a distal end thereof;
wherein the protective sleeve arrangement comprises at least two sleeves being telescopically displaceable in relation to each other and wherein the protective sleeve arrangement is transformable between a retracted position and an extended position,
wherein every sleeve being arranged outwardly of any other of the at least two sleeves comprises an inward protrusion at or in the vicinity of a distal end, and wherein every sleeve being arranged inwardly of any other of the at least two sleeves comprises an outward protrusion at or in the vicinity of a proximal end.

19. A method for preparing a urinary catheter for use, comprising:
providing a urinary catheter having a proximal part with an insertion tip, a distal part and a tubular shaft extending there between in a package with a first compartment having an opening, wherein at least the distal part of the urinary catheter forms an extending part extending out from the package through said opening, and wherein the part of the urinary catheter arranged in the package is arranged in a curved or curled state during storage; and
providing a protective sleeve arrangement arranged around the distal part of the urinary catheter, a proximal end of the protective sleeve arrangement releasably connected to the first compartment, at or in the vicinity of said opening, and a distal end of the protective sleeve arrangement connected to the urinary catheter, at or in the vicinity of a distal end thereof, wherein the protective sleeve arrangement comprises at least two sleeves being telescopically displaceable in relation to each other, wherein the protective sleeve arrangement is transformable between a retracted position and an extended position;
pulling said catheter out from said protective sleeve arrangement, and upon continued pulling, pulling said sleeves apart, thereby expanding the protective sleeve arrangement into its extended position; and
releasing the protective sleeve arrangement from the package, thereby releasing the catheter from the package, whereby the extended protective sleeve arrangement forms a protective cover over at least a part of the length of tubular shaft of the catheter.

\* \* \* \* \*